United States Patent [19]

Whiteneir

[11] Patent Number: 4,660,829

[45] Date of Patent: Apr. 28, 1987

[54] BODY JOINT POSITION MONITORING SYSTEM

[76] Inventor: Paul J. Whiteneir, 2060 Chase, Apt. 2B, Chicago, Ill. 60645

[21] Appl. No.: 753,018

[22] Filed: Jul. 8, 1985

[51] Int. Cl.⁴ ............................................. A63B 69/38
[52] U.S. Cl. ............................. 273/29 A; 273/186 R; 273/183 B; 273/54 B; 901/47
[58] Field of Search ......................... 272/DIG. 5, 143; 273/54 B, 29 A, 183 A, 186 R, 183 B, 189 R, 189 A; 434/247, 249, 252; 250/215; 902/46, 47; 128/25 R, 186 A

[56] References Cited

U.S. PATENT DOCUMENTS

| 3,350,100 | 10/1967 | Carmines | 273/54 B |
| 3,861,688 | 1/1975 | Butler | 273/186 A |
| 3,929,335 | 12/1975 | Malick | 128/25 R X |
| 4,119,212 | 10/1978 | Flemming | 73/1 E |
| 4,250,378 | 2/1981 | Mutton | 250/221 |

Primary Examiner—Richard C. Pinkham
Assistant Examiner—Stuart W. Rose
Attorney, Agent, or Firm—Wood, Dalton, Phillips, Mason & Rowe

[57] ABSTRACT

A body joint monitoring system employs a pair of members adapted to be attached to a pair of adjacent body portions interconnected by a body joint. A position sensing arrangement generates an electrical signal indicative of the position of the first member position relative to the position of the second member. Control circuitry response to the electrical signal to generate a human-sensible signal.

14 Claims, 13 Drawing Figures

BODY JOINT POSITION MONITORING SYSTEM

TECHNICAL FIELD

This invention relates generally to a system for monitoring body joint position, and it more particularly relates to a method and apparatus for monitoring displacement of joints along a three-dimensional path of travel.

BACKGROUND ART

There have been many different types and kinds of devices for sensing and indicating proper body position as an athletic training aid. For example, reference may be made to the following U.S. Pat. Nos: 4,502,035; 3,206,200; 4,193,065; 4,163,552; 2,191,683; 3,156,211; 3,860,245; and 3,861,688.

These devices share the objectives of indicating body position as an athlete's training aid, but they suffer from certain drawbacks. One drawback of some existing designs is the need for the athlete to visually notice an indicator device. This results in concentration being directed away from the requirements of the athlete's sport, so that the device is difficult to use and prone to give erroneous results. Consequently, it is desirable to have a device that does not require visual attention by the athlete to notice deviations from correct body position.

Some existing devices are relatively bulky. They attach to the athlete's body or clothing, and their bulk interferes with the athlete's body movements. Also, many devices project outwardly from the athlete's body or attach to the person of the athlete in some other way that diverts concentration away from the task at hand, with a resulting uneasiness in the athlete apt to develop. So, it is desirable to have a device that is light, non-bulky, and less obtrusive.

Furthermore, existing devices are often incapable of sensing and indicating small deviations from a correct body joint position while providing real time feedback to the athlete. In sports such as tennis and golf, the precise positioning of various joints in the body (particularly the wrist) is essential to perform in a highly proficient manner. And, consequently, it is desirable to have a device that would feed back to the athlete a real time indication of any deviations from a desired joint position so it could be analyzed by the athlete, who could then correct the body position accordingly. In this manner, the athlete can train to execute the body motions required for a highly proficient performance.

In addition, many devices have been suited for one particular sport only. Thus, it would be desirable to have a device that could be used to monitor joint position and associated body position in various sports, while being relatively inexpensive to manufacture and easy to use without undue interference with the play of the game.

Such a method and apparatus should be useful in monitoring robotic, as well as human body joints. In this regard, the inventive system should also be utilized for monitoring the movement and positioning of joints and other portions of electromechanical robots.

Such an inventive system should also be adapted for use in physical rehabilitation of people who have sustained injuries to muscles and other parts of their body. Such a system should provide little or no interference with the movement of the body joints, and yet the retraining of people in the proper movement of their body joints, is facilitated greatly.

DISCLOSURE OF INVENTION

Therefore, an object of this invention is to provide a new and improved body joint monitoring system which facilitates the precise and accurate detection of body movement away from a desired positioning during the play of an athletic event, and which has little or no adverse affect on the athlete's ability to play the game.

It is another object of the present invention to provide such a system that does not require the athlete to direct visual attention to an indicator device.

It is a further object of the present invention to provide such a system capable of real time feedback to the athlete of deviations from desired joint position, and to provide a relatively inexpensive system that is light in weight, adaptable to various sports, and less apt to distract the athlete during execution of the game so that it does not tend to interfere with performance, or restrain the movement of the joint. Alternately, the first member of the invention and the second member may both connect to various locations on the same body portion in the case of some types of body joints. For example, as in the case of the elbow joint, it is possible to sense the degree of bend in the elbow joint by attaching both members of the invention to selected parts of the same forearm.

The above and further objects of the present invention are realized by providing a system that employs a first member adapted to be attached to a first one of a selected pair of body portions at a body joint, And a second member that is connected to the other one of the pair of body portions.

A position sensing device is included for generating an electrical signal indicative of the position of the first member relative to the position of the second member. A circuit device responds to the electrical signal for generating a corresponding human-sensible signal.

In one form of the invention, a light-emitting diode and phototransistor combination are mounted on one of the members to serve as an optical sensing device for sensing the relative position between the members. One member is placed around a tennis player's forearm, and the other member is attached to the wrist. Audible tones are generated and supplied to a headset to indicate any deviation from correct wrist position.

Thus, real time feedback of small deviations in joint position, such as the position of the wrist relative to the forearm, is provided that does not require the athlete's visual attention. The system is light in weight and is easy to use. It is adaptable to various sports and to other joint monitoring uses, such as robotics and physical rehabilitation and the like, as well as being relatively attractive and relatively inexpensive to manufacture.

BRIEF DESCRIPTION OF THE DRAWINGS

The above and other objects and many features of the invention will become more apparent, and the invention itself will be better understood, upon reading the following detailed description in conjunction with the accompanying drawings, wherein.

DETAILED DESCRIPTION

Figures 1, 3:
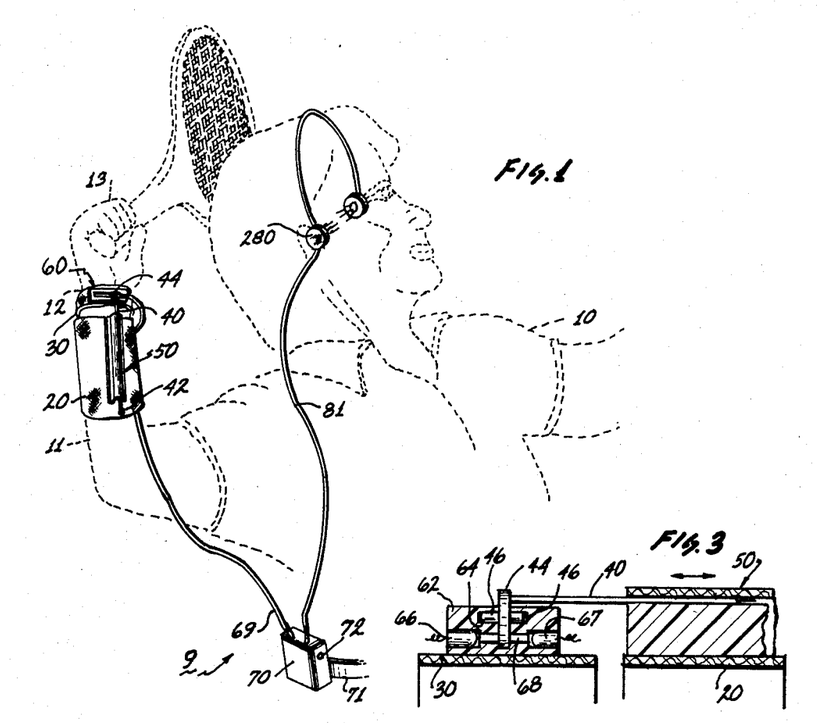
FIG. 1 is a pictorial view of a monitoring system which is constructed according to the present invention, and which is illustrated in use by an athlete.
FIG. 3 is a greatly enlarged sectional elevational view of the portion of the system of FIG. 2 taken on line 3—3 of FIG. 2.
Figure 2:
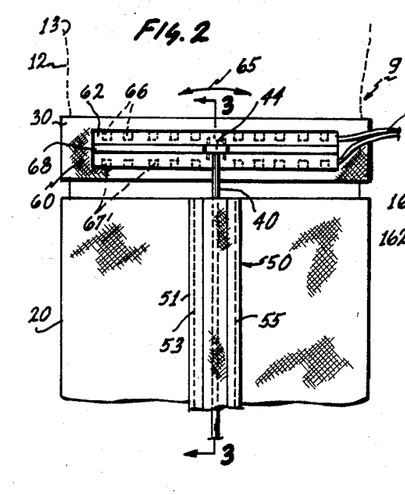
FIG. 2 is an enlarged fragmentary plan view of a portion of the system of FIG. 1, mounted on the wrist and forearm of the athlete.

Turning now to FIGS. 1-3 of the drawings, there is shown a body joint position monitoring system, generally indicated at 9, which is constructed according to the invention, and which is illustrated in place on a tennis player 10. The system 9 is designed to monitor the relative position of a pair of body portions, such as the wrist joint 12 and the forearm 11.

While a tennis aid is shown and described herein, it will become apparent to those skilled in the art, after a review hereof, that the system of the present invention may also be used in other sports, such as bowling and others. Moreover, the inventive system may also be employed in other fields, such as robotics and physical rehabilitation.

The system 9 includes a pair of harness members 20 and 30. Each one of the harness members is shown attached to a corresponding one of the selected pair of the body portions. The first harness member 20 is secured to the forearm portion 11, and the second harness member 30 is attached to the wrist portion 12.

Each one of the harness members of the system 9 is composed of an elastic band and is shaped and dimensioned to enable easy but secure placement encircling the respective body portion. They can be slipped on over hand 13 of the tennis player. The system 9 serves the function of establishing a stationary reference point on the body portion 11 so that the relative position between the wrist portion 12 and this reference point can be monitored.

Other harness members that serve this function may also be employed within the inventive concepts herein disclosed. For example, a self-adhesive piece of tape may be employed as discussed further with reference to FIG. 10-12.

A rigid extension element 40 in the form of a stiff wire, having a first or rear end 42 and a second or front end 44, is affixed by attachment arrangement 50 to the first harness member 20. The extension element is attached so that the second or rear end extends in substantially fixed alignment with the first harness member to a relatively stationary position along the second harness member on the upper forearm. Sensor device 60 senses the position of the front end 44 relative to the wrist harness member, and generates an electrical signal indicative of the relative position between the wrist harness member and the forearm harness member. Thus, this electrical signal is also indicative of relative position of the joint, and thus is indicative of the amount of wrist rotation relative to a certain desired reference point.

The electrical signal is coupled by suitable means, such as cable 69, to control circuitry within a control module 70. Module 70 is turned on and off by a switch 72, and the circuitry therein generates a driver signal that is coupled to headset 80 by suitable means such as cable 81, to provide a human-sensible signal corresponding to the electrical signal.

Thus, movement of the joint interconnecting forearm portion 11 and wrist portion 12 is converted to a corresponding electrical signal, which is then converted to an audible signal to provide real-time feedback to the tennis player of any deviations in wrist joint position from the desired position. The system accomplishes this function without requiring the tennis player's visual attention. Also, it does it with a light-weight, aesthetically-pleasing device that does not impair the tennis player's performance. Furthermore, the inventive concept is readily adaptable to joint monitoring requirements of other sports and uses as well.

Referring to FIGS. 2 and 3, sensor device 60 includes a strip 62 that defines a groove 64. The front end 44 of extension element 40 is in the form of a slider block, which includes a pair of ears 46 (FIG. 3) extending on opposite sides thereof to engage groove 64 slidably. This arrangement enables wrist portion 12 to rotate in the direction, back and forth, as indicated by arrow 65 (FIG. 2), with the front end 44 of the extension element sliding along groove 62 to various positions along the wrist harness member.

A series of like-numbered light-emitting diodes 66 are disposed at spaced-apart intervals along strip 64 on one side of the groove, and a corresponding series of phototransistors 67 are disposed at corresponding spaced-apart intervals along the other side of the groove. The light-emitting diodes and phototransistors are arranged in pairs to define a series of equally spaced apart light paths, of which one is designated reference numeral 68. As the front end 44 slides along the groove 62, the end 44 blocks corresponding ones of the light paths so that the output of the blocked phototransistors 67 provides an electrical signal indicative of the position of the front end 44 and, therefore, of the relative positioning of the first and second harness members.

Attaching arrangement 50 comprises a strip 51 of flexible material secured over the extension element 42 to the forearm harness member 20 by suitable means such as stitching at 53 and 55 along the opposite marginal edges thereof. This attaches the rear end portion 42 of extension element 40 to forearm harness member 20, so that the extension element is retained in substantially fixed alignment with its forearm harness member, while enabling the extension element to slide relative thereto.

Figure 4:
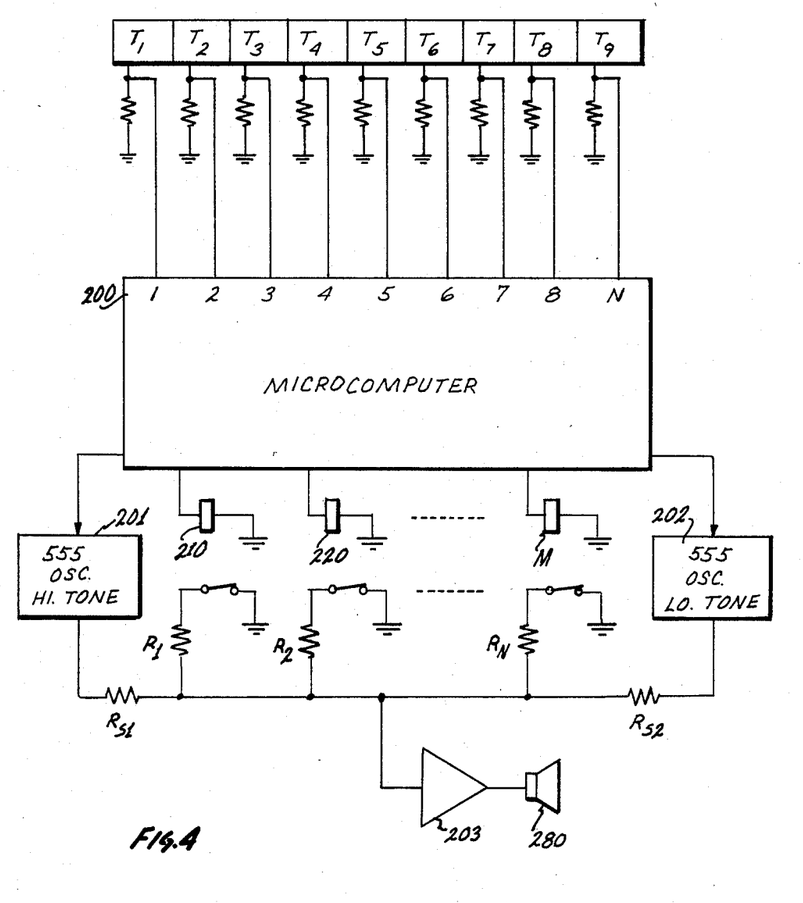
FIG. 4 is a partly schematic block diagram of the circuitry employed in the system of FIG. 1.

Turning now to FIG. 4, there is shown a schematic diagram of suitable circuitry, constructed in accordance with the invention, for receiving an electrical signal from the sensor device and for generating a corresponding human-sensible signal. This circuit employs a conventional microcomputer component of the type commonly available, along with programs, for the microcomputer using known means.

The circuit receives an output signal from each of the series of phototransistors 67. In FIG. 4, the phototransistor positions are designated T1 through $T_N$. The output of these phototransistors are transmitted over a corresponding number of lines to inputs 1 through N of microcomputer 200 using techniques known in the art.

Microcomputer 200 is suitably programed to turn on either high-tone oscillator 201, or low-tone oscillator 202, according to the signals received from the phototransistors. When any one of the phototransistors to one side of a selected reference position is turned off by the second end of the extension element blocking the corresponding light path, oscillator 201 is activated. When any of the other phototransistors on the other side of the selected reference position are turned off, oscillator 202 is activated. The output of high-tone oscillator 201 and low-tone oscillator 202 are coupled through source resistors $R_{s1}$ and $R_{s2}$ to audio amplifier 203 which amplifies the signal to drive headsets 280.

Thus, a different tone is produced to designate joint positioning relative to a desired "center" reference position. The center reference position is stored in the memory (not shown) of the microcomputer, and then compared with the present position.

In this regard, before commencing operation, an ON-OFF switch (not shown) is closed to activate the system. Thereafter, an initialization switch 72 (FIG. 1) is closed, according to an initialization procedure for storing in the memory the desired reference position of the joint (wrist) at that moment. Thus, the user holds and positions the racket in the desired manner, in one hand, and then closes the switch 72 with the other hand to record the desired position of the joint Thereafter, when play commences, the microcomputer determines any deviation from the stored reference position to cause the generation of the appropriate audible tone, according to the amount of deviation from the reference position.

Microcomputer 200 is also suitably programmed to adjust the volume of the audible tone generated by headset 280, according to how far the joint position has deviated from the center reference position. This is done by operating the appropriate one of a series of relays, thereby to ground the corresponding one of resistors R1 through $R_n$. Relays 210 and 220, of a series up to relay M, are illustrated in FIG. 4 along with the corresponding resistors $R_1$ and $R_2$ of a corresponding series of resistors up to $R_N$ (M=N). The grounded resistor forms a voltage divider network with resistor $R_{s1}$ or $R_{s2}$ to vary the magnitude of the input to audio amplifier 203 and thereby vary the audio output from headset 280.

The microcomputer is programmed to cause the high-tone to activate if the harness members are rotated in a first direction relative to a specified reference position, and to cause the low-tone oscillator to activate if the harness members are rotated in the other direction relative to the specified reference position. The volume of the tone can be adjusted to provide an audible indication of the amount of deviation from the reference position.

FIGS. 5-8 combine to form a flow diagram describing programming employed for the system 9. This flow diagram may be implemented using programming techniques well known in the art to enable the microcomputer to function in the manner described.

Figure 5:
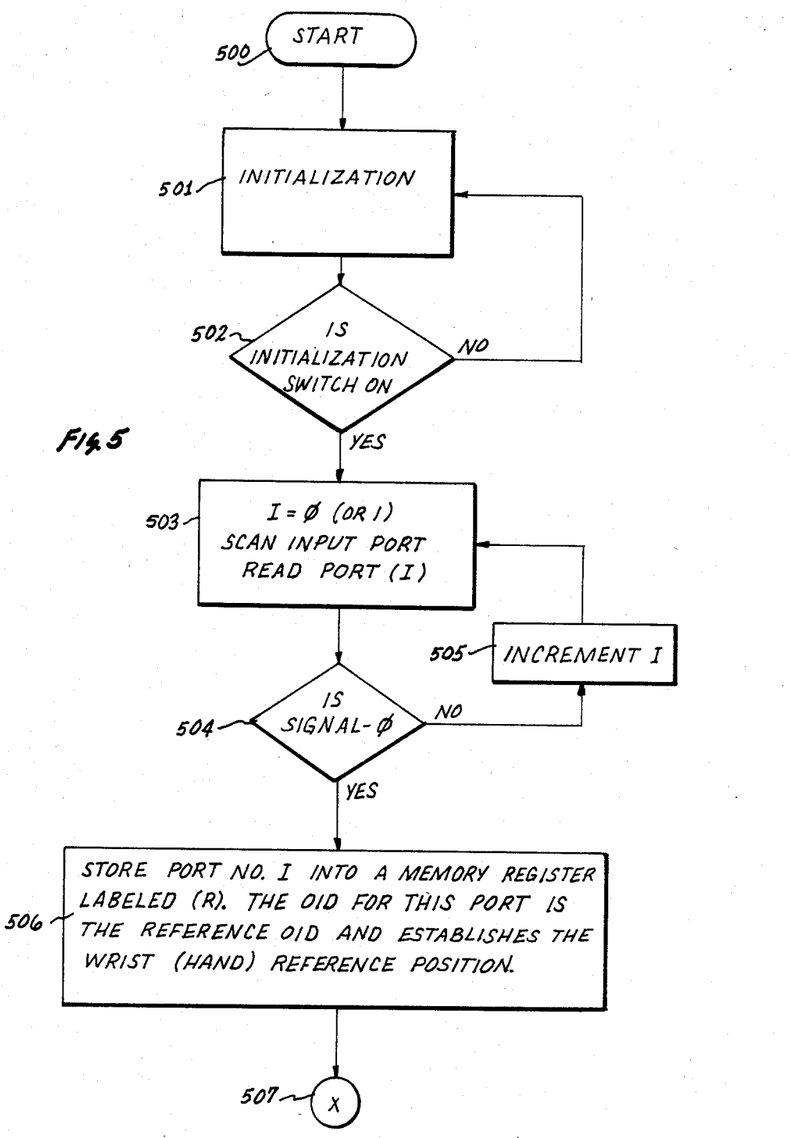
FIGS. 5-8 and 8a combine to form a flow diagram of a computer program employed in the circuitry of FIG. 4.
Figure 6:
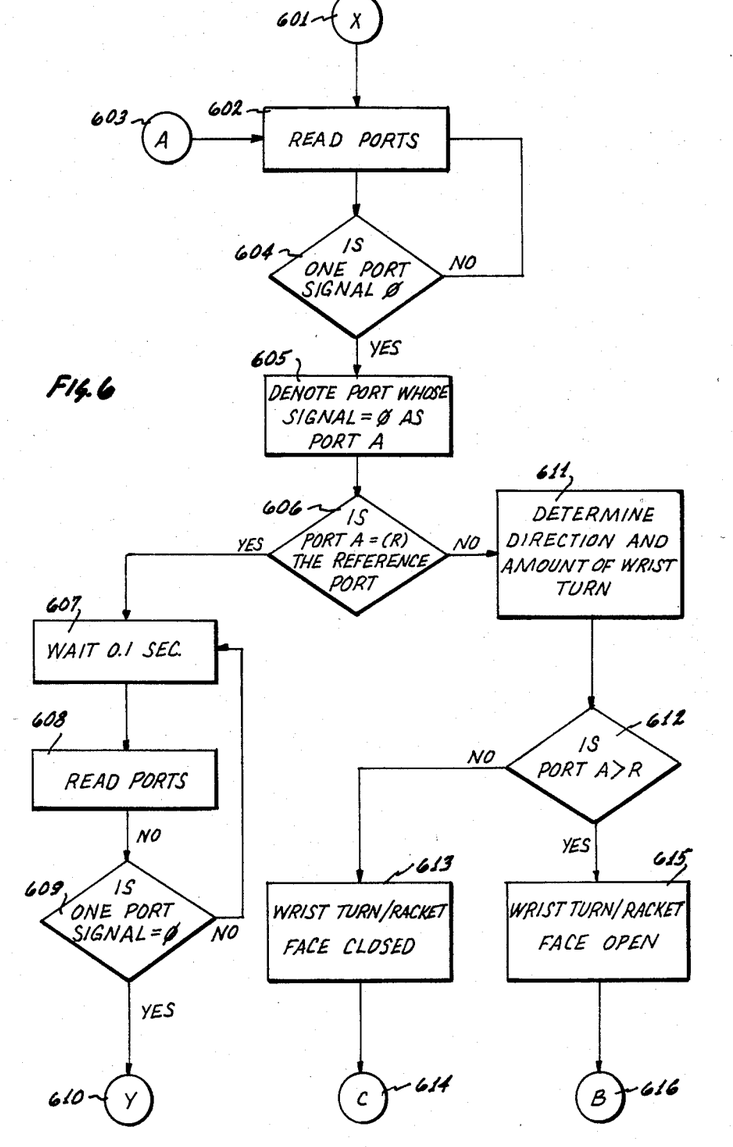

As indicated in FIG. 5, block 500, the program starts through an initialization process that includes a check of the status of switch 72 on module 70. After the switch is turned on and the program is initialized, including a scan of the input ports and the determination of the "center" reference position, the desired reference position of the joint at the moment the initialization switch 72 is closed momentarily. Thus, a "center" reference port is established and stored in the memory of the microcomputer.

Thereafter, as indicated in blocks 501 through 506, the program proceeds to read the input ports every 0.1 seconds. When one of the light paths corresponding to the reference port, other than the referenced light path is blocked, the decision represented by block 606 in FIG. 6 initiates programming steps to determine the amount of the wrist turn and whether the wrist is turned in one direction (racquet face closed), or the other direction (racquet face open), as indicated in blocks 611-615.

Figure 7:
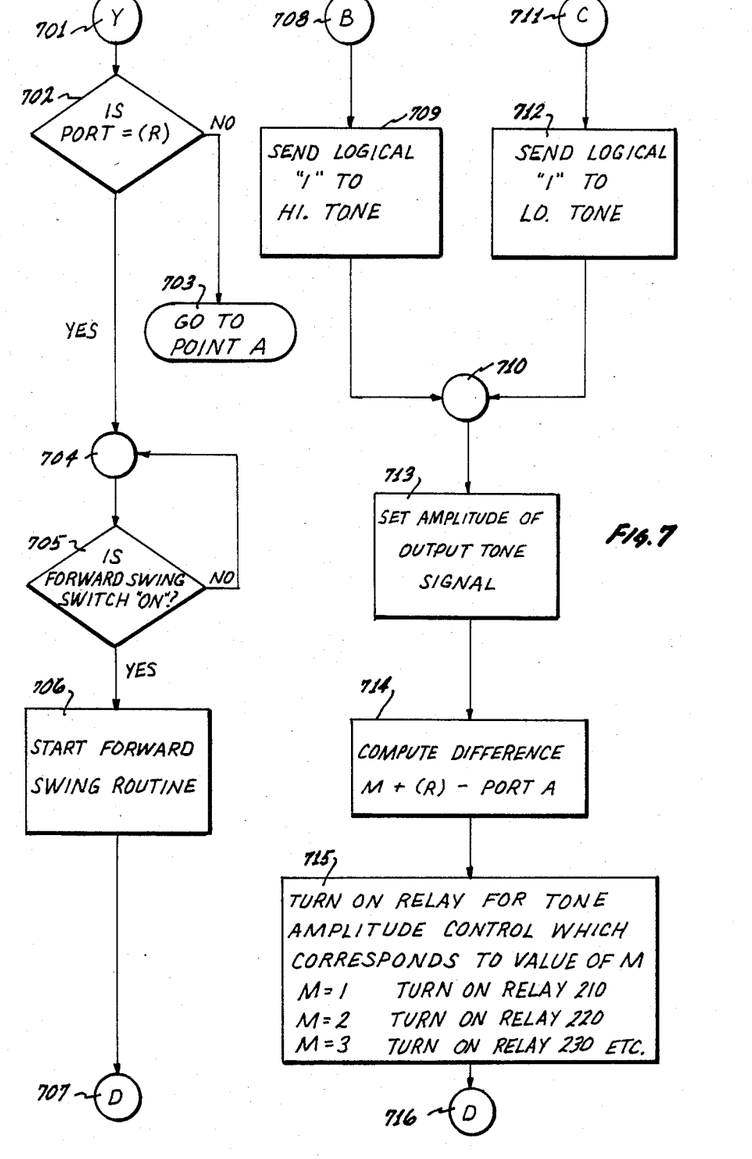

As shown in the portion of the flow diagram shown in FIG. 7, the program proceeds from junction point B, block 708, to set a high tone and to set the amplitude according to how far the relative position is from the reference position. From junction point C, block 711, the low tone is set and then the amplitude set accordingly (block 710-715).

Figure 8:
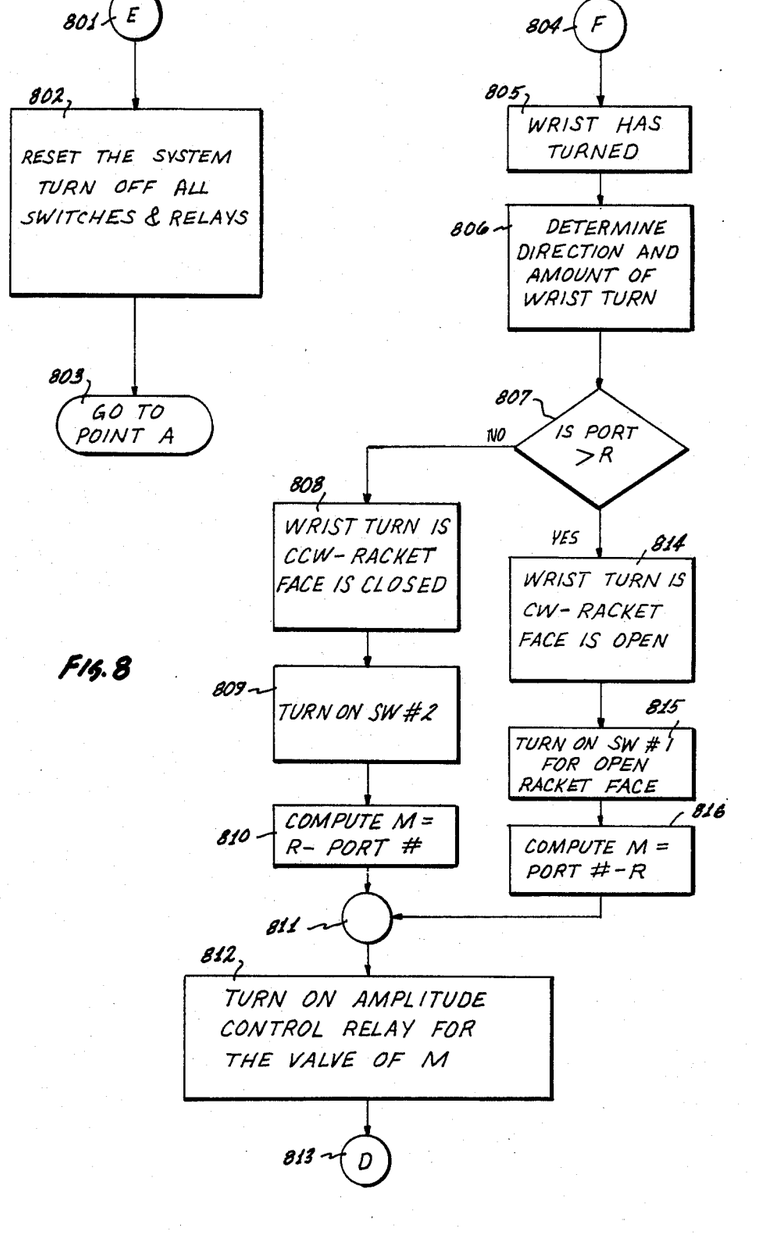

FIG. 8, blocks 804-812, show the steps involved in setting the tone amplitude. Thus, block 807 determines whether a port that is blocked is one side or the other side of the center reference port, turns on the face-closed switch, or face-open switch accordingly, and turns on the amplitude control relay corresponding to the relative deviation from the center reference position. Thus, the appropriate tone is supplied to the headset 280 (FIGS. 1 and 4) to alert the user to the quantitative amount of deviation from the desired reference position stored in the memory.

Figure 8A:
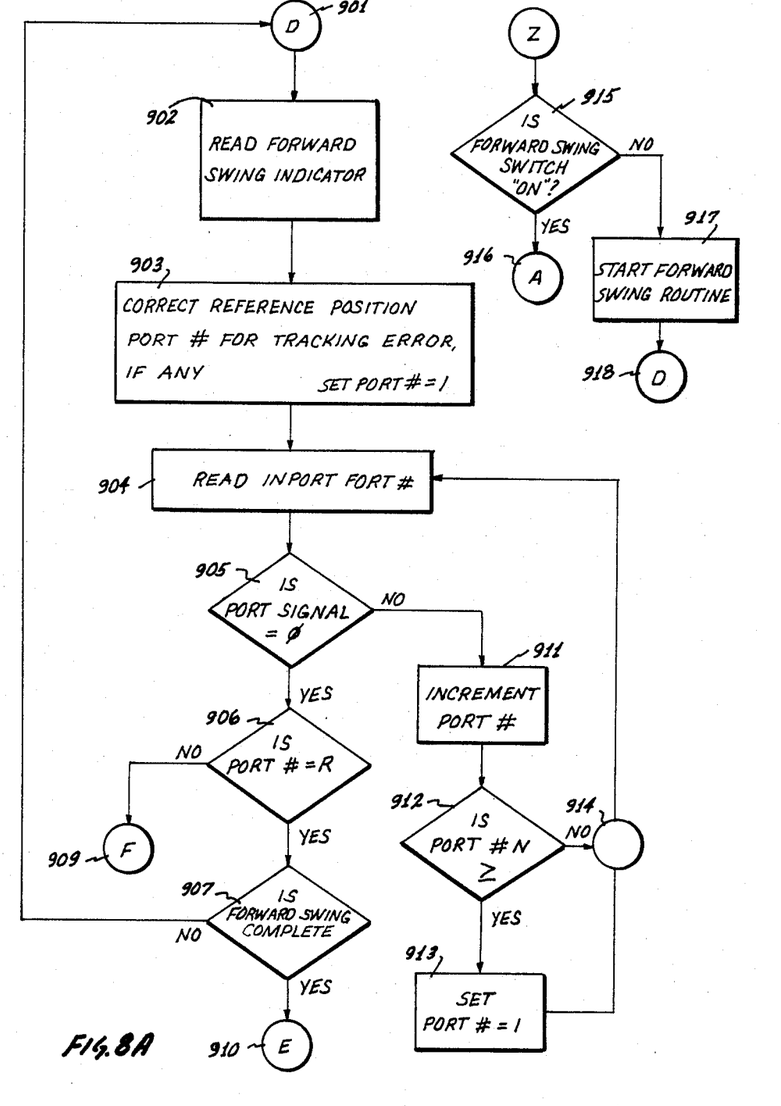

FIG. 8A shows a sub-routine, blocks 901-914, that loops until there is a deviation from the center reference position, at which time it exits to point "F." This sub-routine features the ability to read a forward swing indicator switch (not shown), block 902, and exit to point "E" when the forward swing is completed. Where a forward swing switch is not included, such as in the system illustrated in FIG. 1, block 907 can be suitably bypassed.

In operation, module 70, with the programmed microcomputer and associated circuitry within, is battery powered for portability and provided with suitable means for attaching to the athlete, such as means (not shown) to clip it to the athlete's belt 71. Headset 80 is put in place on the athlete's head and connected to the module by cord 81. The first and second harness members are slipped on over the hand 13 to the appropriate positions on the wrist and forearm of the athlete, and with the wrist in the proper position, the on-off switch is turned to the on position. This position of the wrist is recorded by the microcomputer as the center reference position, and any deviations from this reference position are converted to a variation in the tone and loudness of the audible signal produced by the headset. Thus, an audible signal is produced and its attributes varied to provide real-time feedback to the athlete of any deviations in joint position from a selected reference position.

Figure 9:
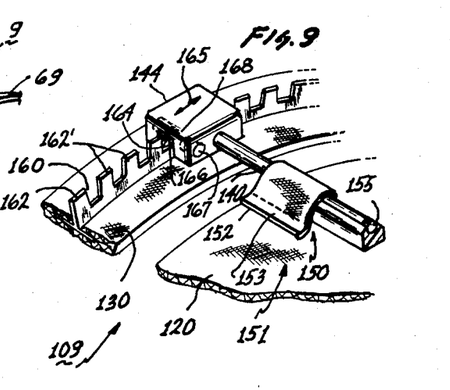
FIG. 9 is a pictorial, fragmentary view of a portion of a monitoring system, which is constructed according to the invention, and which employs an alternate means of position sensing.

Referring to FIG. 9, wherein reference numerals are increased by one hundred over those designating similar components in FIGS. 1-3, there is shown a body joint position monitoring system 109, which is also constructed according to the present invention. The system 109 includes the various components of the system 9 of FIG. 1, except the manner of interrupting the spaced-apart light paths. An attaching arrangement 151 includes a piece of flexible material 152 attached by stitches 153 to first or forearm harness member 120. An extension element 140, in the form of a rigid wire, fits within an extension element 140 groove 155 of a guide block 154.

The system 109 includes a sensor device 160, which includes a radially-extending strip 162 for blocking the light paths as the wrist of the user rotates away from a desired reference position. The front end 144 includes a groove 164 in which strip 162 slides. Pair of light-emitting diodes 166 and phototransistors 167 define light paths 168 extending across the groove. A series of spaced-apart radially-extending tabs designated by like reference numerals 162' block light paths 168 as the front end 144 slides along strip 162. Light-emitting diodes 166 and phototransistors 167 thereby generate an electrical signal which is transmitted over a suitable cable (not shown) to a control module (not shown).

Figures 10, 11:
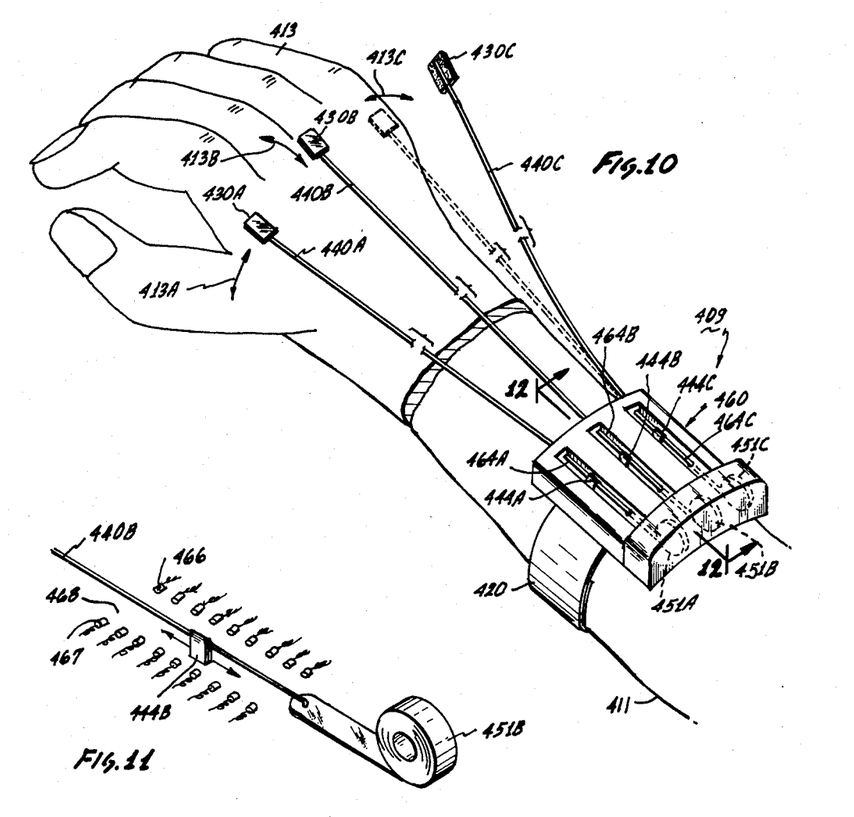
FIGS. 10-12 are pictorial views of yet another monitoring system, which is constructed according to the present invention.
Figure 12:
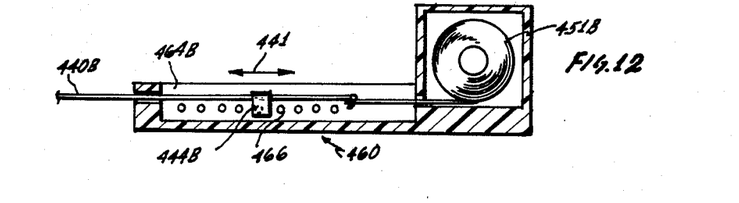

In FIGS. 10 through 12 there is shown a monitoring system 409, which is also constructed in accordance with the present invention. This system is similar to the system 9 shown in FIG. 1, except that it employs a different form of light path interrupters and monitors two additional body motions.

The system generally comprises a sensor device 460 strapped with first member 420 to the forearm 411 of the user with first member 420, and it employs a series of three flexible lines, 440A, 440B and 440C (nylon monofilament fishing line), which have their distal ends secured to the various portions of the hand 413 by means of adhesive pads, second members 430A, 430B and 430C. Three lines are shown, but more or less may be used depending on the application of the invention.

As shown in FIG. 11, sensor device 460 includes a series of pairs of phototransistors 466 and light-emitting diodes 467 that provide a series of spaced-apart light paths 468 similar to the device 60 of FIG. 1. Light-blocking devices 444A, 444B and 444C, attached to the respective lines 440A, 440B and 440C, are disposed in grooves 464A, 464B and 464C in the face of sensor device 460.

In order to maintain the lines taut, three negator springs, 451A, 451B and 451C, are mounted in the rear end of the sensor device attached to rear ends of the three lines. Then a control circuit (not shown) responds to signals from the phototransistors in a similar manner as the control circuit shown in FIG. 4. In place of the springs, small DC motors (not shown) may also be employed.

The device attached to each line is preferably in the form of a piece of opaque paper which is folded over and secured together by means of suitable adhesive The width of the paper is sufficient to block the light path between one pair of the phototransistors and light-emitting diodes. Thus, as line 440B moves in the direction of arrow 441 (FIG. 12), the light path corresponding to the position of pad 430B relative to strap 420 is blocked. This technique allows monitoring rotational hand movement depicted by arrow 413A in FIG. 10, as well as up-and-down movement (arrow 413B) and side-to-side movement (arrow 413C).

Flexible lines, 440A, 440B, and 440C are used, such lines do not tend to inhibit the movement of body portions. Unlike rigid members and the like, flexible lines are not a safety hazard to the users of the invention. This feature is particularly important to athletes or those who are subject to tripping and possibly falling onto the device, thereby causing injury Users of the invention for physical rehabilitation training, who have had certain types of physical injuries, particularly benefit from the use of flexible lines, since such persons may well be prone to falling.

After a review of the foregoing, it will become apparent to those skilled in the art, that the system of the present invention provides a means for measuring displacements along a three-dimensional path. The path may well be pure linear, pure rotational, or a curvilinear excursion. In this regard, the inventive system measures or determines the length of the excursion along any three-dimensional path, even though the path is totally randomly occurring in time, and in no manner predictable or ascertainable in advance. As previously described, the incremental measurement is achieved by determining the number of light paths interrupted as a result of a given excursion. By knowing the various parameters of a given excursion, the microcomputer 200 can be programmed to track or measure the amount of the displacement, and generate an output signal indicative of such an amount. The flexible line enables the body to move in a curvilinear manner, and cause a measurement to be sensed as the flexible lines follow such motion.

It should also be understood that no portion of the system need extend across a body joint to sense its position or extent of movement. Thus, the inventive system has little or no affect on the movement of the joint. For example, the first and second members of the system can be affixed to the same forearm in a spaced apart manner, and in so doing, the system can measure the extent of bending the elbow.

As various other changes may be made in the form, construction, and arrangement of the procedures and parts described herein, without departing from the true spirit and scope of the present invention and without sacrificing any of its advantages. For example, in place of the plurality of light paths, other position detecting arrangements may be employed, such as potentiometers, Hall effect devices, and magnetic recording heads as used in tape recorders and other such movement sensing gauges, and the like. All matter herein is to be interpreted as illustrative and not in any limiting sense.

What is claimed is:

1. A system for monitoring joint position, comprising:
a pair of first and second members, each one of the members being adapted to be attached to the body in a spaced-apart manner;
position sensing means for generating an electrical signal indicative of a deviation in first member position relative to the second member from a desired relative position;
said position sensing means including a rigid extension element having a first end and a second end, attaching means for attaching the first end of the extension element to the first member so that the second end extends in substantially fixed alignment with the first member to a position along the second member corresponding to a specified relative position of the first and second body portions, and sensor means for sensing the position of the second end;
said sensor means including light generating means for generating light along a series of spaced apart light paths along the second member corresponding to a series of relative member positions, blocking means for causing the second end of the extension element to block a light path corresponding to a specified one of the series of relative member positions when the first and second rembers are in the specified relative member position, and light detector means responsive to a light path being blocked for generating a corresponding electrical signal; and circuit means responsive to the electrical signal for generating a corresponding output signal to enable a user to correct positionally the relative positioning of the first and second body portions.

2. A system as recited in claim 1, wherein:

the light generating means includes a series of spaced apart light emitting diodes attached along the second member; and the light detector means includes a series of phototransistiors, each one of the phototransistors being aligned with a corresponding one of the light emitting diodes to define the series of spaced apart light paths along the second member.

3. A system as recited in claim 1, wherein the sensor means includes:

a series of spaced apart tabs in upstanding positions along the second member that correspond to a series of relative member positions;

positioning means for causing the second end of the extension element to lie adjacent the one of the series of spaced apart tabs that corresponds to a specified one of the series of relative member positions when the first and second members are in the specified relative member position; and tab detector means responsive to the second end of the extension element lying adjacent the tab that corresponds to the specified relative member position for generating a corresponding electrical signal.

4. A system as recited in claim 3, wherein the tab detector means includes:

optical tab detector means attached to the second end of the extension element for defining a light path and generating the electrical signal by detecting when the tab blocks the light path.

5. A system as recited in claim 4, wherein the optical tab detector means includes:

a light emitting diode and phototransistor combination, the combination being attached to the second end of the extension element to define a light path; and guiding means for guiding the light emitting diode and phototransistor combination adjacent the tab that corresponds to the specified one of the relative member positions so that the tab blocks the light path when the first and second harness members are in the specified relative member position.

6. A system as recited in claim 1, wherein the first member includes:

a sleeve member adapted to be attached around a forearm portion of a human body.

7. A system as recited in claim 1, wherein the second member includes:

a wrist band member adapted to be attached around a wrist portion of a human body.

8. A system as recited in claim 1, wherein the position sensing means includes:

a flexible cord extending between the first and second members, the cord having a first end attached to the first member, a second end attached to the second member, and an extension portion having a length extending between the first and second members;

reel means for maintaining the extension portion taut; and length sensing means for generating an electrical signal indicative of the length of the extension portion.

9. A system as recited in claim 8, wherein the second member includes:

a piece of self-adhesive tape adapted to be attached to a portion of the body.

10. A system as recited in claim 1, wherein the circuit means includes:

digital logic means responsive to the electrical signal for generating a driver signal; and transducer means responsive to the driver signal for genrating a corresponding audible signal.

11. A system as recited in claim 10, further including:

varying means for varying an attribute of the audible signal according to first member position relative to the second member.

12. A system as recited in claim 11, wherein the varying means includes:

amplitude varying means for varying the amplitude of the audible signal according to first member position relative to the second member.

13. A system as recited in claim 11, wherein the varying means includes:

tone varying means for varying a tone associated with the audible signal according to first member position relative to the second member.

14. A system as recited in claim 1, wherein said circuit means stores center reference position information according to an initialization operation, and subsequently cause the generation of said said output signal indicative of the amount of deviation detected by said sensing means.

* * * * *